United States Patent [19]

Fujimoto et al.

[11] 4,383,448
[45] May 17, 1983

[54] SEMI-AUTOMATIC SCANNER FOR ULTRASONIC FLAW DETECTION

[75] Inventors: Hirotsugu Fujimoto; Tsutomu Hayashi; Tatsukuma Hosono, all of Hitachi, Japan

[73] Assignees: Hitachi, Ltd.; Hitachi Engineering Co., Ltd., both of Tokyo, Japan

[21] Appl. No.: 184,376

[22] Filed: Sep. 5, 1980

[30] Foreign Application Priority Data

Sep. 7, 1979 [JP] Japan .................................. 54-114252

[51] Int. Cl.³ ............................................ G01N 29/04
[52] U.S. Cl. ...................................................... 73/637
[58] Field of Search ................... 73/622, 637, 638, 640

[56] References Cited
U.S. PATENT DOCUMENTS

| 3,824,843 | 7/1974 | Gebeshuber et al. | 73/640 |
| 3,934,457 | 1/1976 | Clark et al. | 73/637 |
| 4,279,158 | 7/1981 | Kajiyama et al. | 73/637 |

Primary Examiner—Stephen A. Kreitman
Attorney, Agent, or Firm—Antonelli, Terry & Wands

[57] ABSTRACT

A semi-automatic scanner for ultrasonic flaw detection comprises a carriage travelling on a guide rail, a guide arm extending in a direction transverse to the travel direction of the carriage and supported by the carriage so as to pivot in a plane transverse to the travel direction of the carriage, a probe holder slidably supported by the arm, and a probe mounted on said probe holder so as to pivot about two axes transverse to each other. One of the axes is generally in parallel to the travel direction of the carriage. The carriage is driven by a motor, and the probe is moved by manual or motor-driving operation in a direction transverse to the travel direction of the carriage while pressing the probe on a surface to be inspected, whereby the probe accurately follows the surface even if the surface is curved.

10 Claims, 13 Drawing Figures

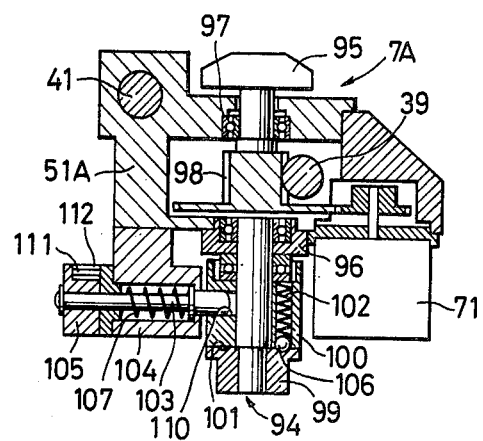
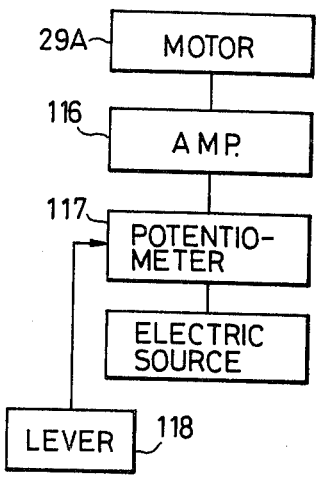
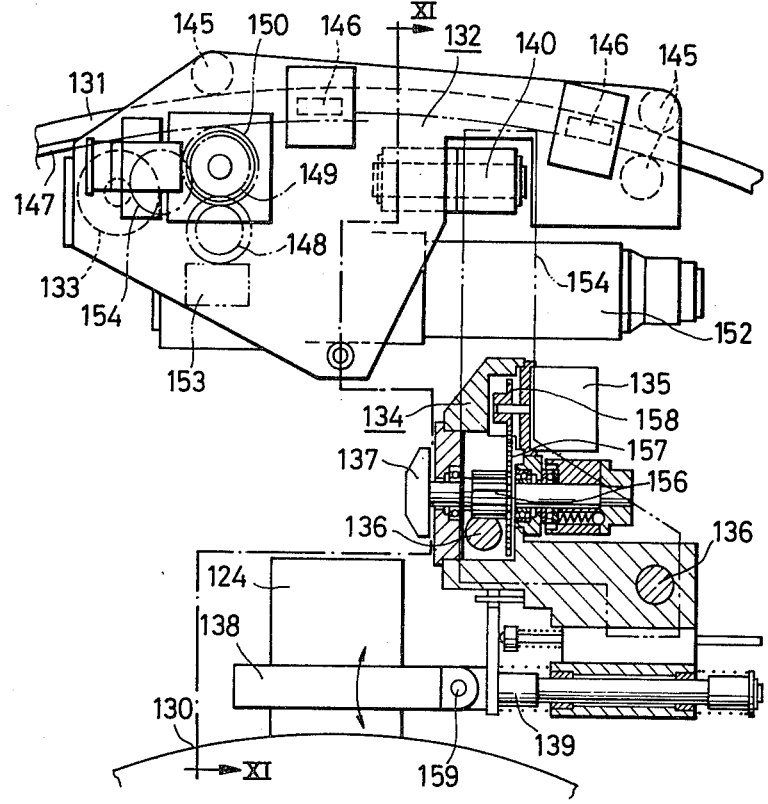

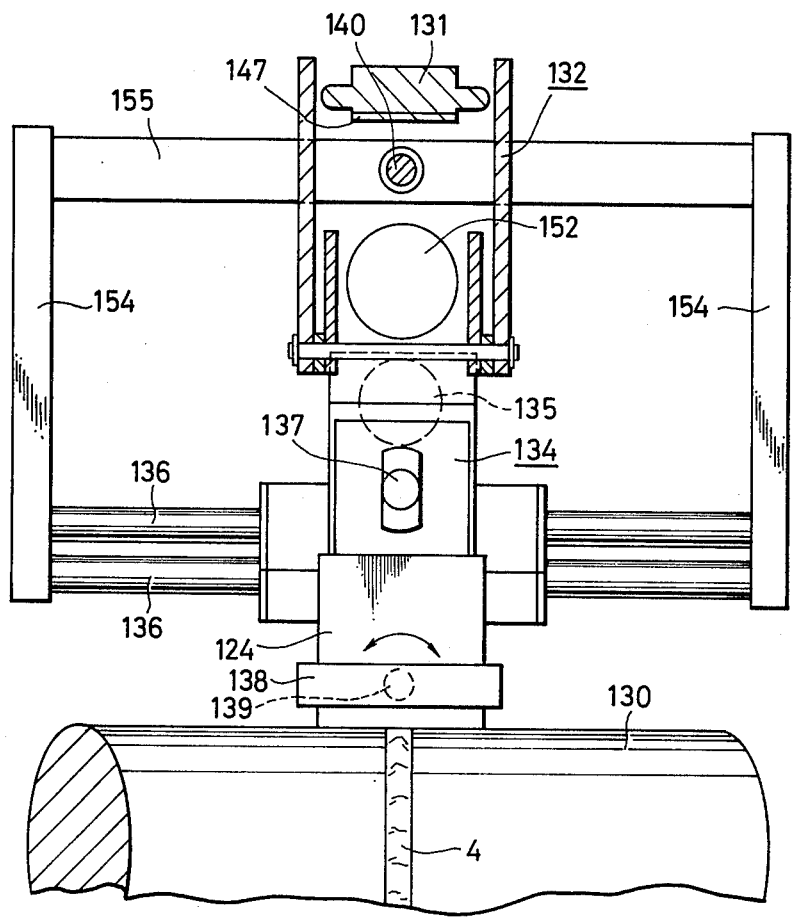

SEMI-AUTOMATIC SCANNER FOR ULTRASONIC FLAW DETECTION

BACKGROUND OF THE INVENTION

This invention relates to a semi-automatic scanner for ultrasonic flaw detection, and more particularly to a scanner which can satisfactorily perform also the inspection of a curved surface in a bent piping.

A conventional scanner or ultrasonic flaw detector is disclosed in Japanese Laid-open Patent Application No. 52-108874. The detector comprises a carriage travelling on a guide rail mounted on a pipe, a guide rod mounted on the carriage and extending in the axial direction of the pipe, an inspection arm mounted so as to move along the guide rod and extending perpendicularly to the surface of the pipe, and a probe mounted on the end of the inspection arm so as to contact the surface to be inspected. In the ultrasonic flaw detector, the probe suitably follows the surface of a straight pipe shown in FIG. 1 of the above mentioned document, through the peripheral movement of the carriage as well as the guide rod, the axial movement of the inspection arm, and the movement of the probe perpendicular to the surface to be inspected of the pipe. However in a case where the ultrasonic flaw detector is employed to inspect the curved surface part of a bent pipe, the probe does not properly follow the curved surface.

In pipings to be inspected in a nuclear power plant, there are more bent pipe portions than straight pipe portions and much time is needed for inspecting such a bent pipe portion. Therefore, there scanners or ultrasonic flaw are desired which can satisfactorily perform also the inspection of the curved surface portions of bent pipings.

SUMMARY OF THE INVENTION

An object of the invention is to provide an ultrasonic flaw detector or scanner, in which a probe can follow satisfactorily a curved surface such as a bent pipe.

Another object of the invention is to provide an ultrasonic flaw detector or scanner, wherein a probe can move to cover all the surface to be inspected including a curved surface of a bent pipe, and which can trace the track of the probe even if it is operated manually.

A further object of the invention is to provide an ultrasonic flaw detector or scanner which can perform an accurate inspection with manual operation.

Still another object of the invention is to provide an ultrasonic flaw detector or which can detect flaws in the curved surface such as a bent pipe without requiring a large area for installing the detector on the bent pipe.

Briefly stated, the invention resides in a semi-automatic scanner for ultrasonic flaw detection comprising a carriage travelling on a guide rail, a guide arm extending in a direction transverse to the travel direction of the carriage and mounted on the carriage so as to pivot or swing in a plant transverse to the travel direction, a probe holder slidably mounted on the guide arm, and probe pivotably held by the probe holder so that the probe follow a curved face to be inspected.

BRIEF DESCRIPTION OF THE ACCOMPANYING DRAWINGS

FIG. 8 is a sectional view of another embodiment of a probe holder employed in a scanner according to the invention;

FIG. 9 is a block diagram an embodiment of a motor driving a circuit employed in a scanner according to the invention;

FIG. 10 is a sectional view of another embodiment of a scanner according to the invention;

FIG. 11 is a sectional view of a scanner taken along a line XI—XI of FIG. 10;

DESCRIPTION OF THE PREFERRED EMBODIMENTS

Referring to the accompanying drawings, an embodiment of a semi-automatic scanner for ultrasonic flaw detection according to the invention will be described hereinafter in detail.

Figure 1:
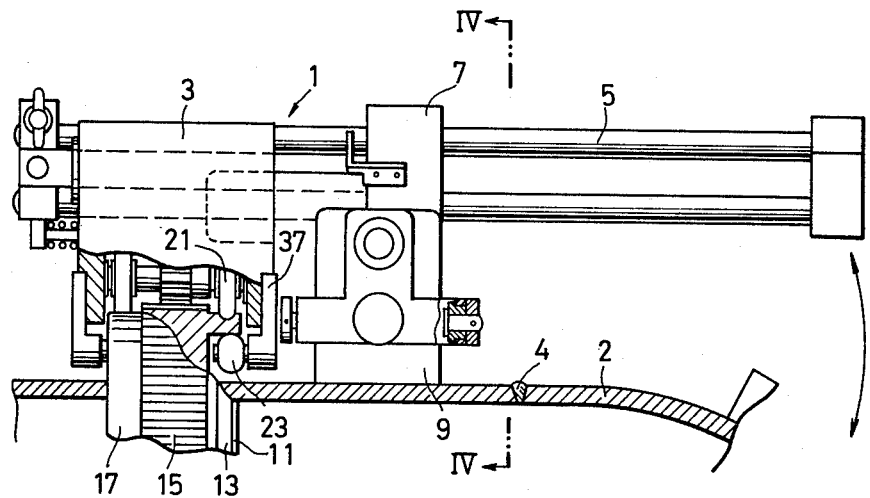
FIG. 1 is a sectional front view of an embodiment of a scanner according to the invention.

In FIG. 1, the scanner or ultrasonic flaw detector 1 comprises a carriage 3, a guide arm 5 supported by the carriage 3 to move along with the carriage 3, a probe holder 7 mounted slidably on the guide arm 5, and a probe 9.

The carriage 3 is fitted on a guide rail 11 so as to travel thereon. The guide rail 11 is mounted coaxially on a pipe 2 to be inspected, and has a guide groove portion 13, a rack 15, and a supporting portion 17, each formed thereon. The carriage 3 is provided with front rollers 21 fitted in the groove 13, and back rollers 23 pressing against the backside of the groove portion 13, which back rollers 23 each are mounted rotatably on brackets 37. A plurality of pairs of the rollers 21 and 23 sandwich the guide rail 11 so that the carriage 3 can not be dismounted from the guide rail 11.

Figure 3:
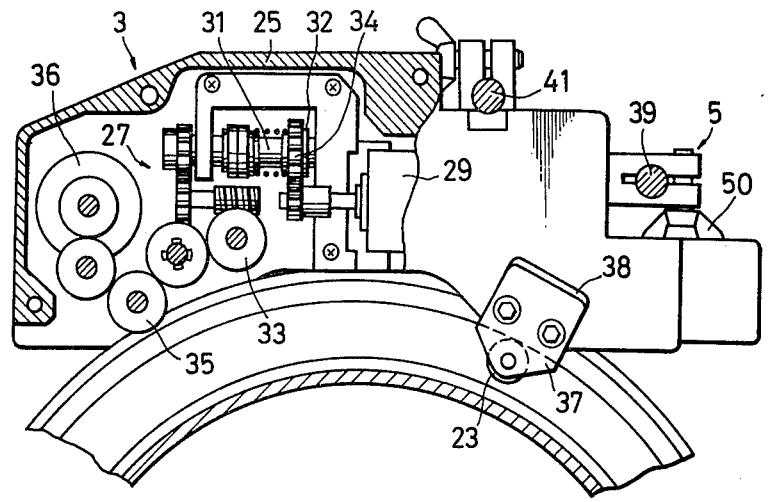
FIG. 3 is a sectional view of a carriage employed in the scanner shown in FIG. 1.

The carriage 3 will be described more in detail. In FIG. 3, the carriage 3 has a housing 25 somewhat extending circumferentially and supporting thereon the guide arm 5 as previously stated, and a driving apparatus 27 in the housing 25. The driving apparatus 27 comprises a motor 29, a safety device 31 connected to the motor 29 by gear means, reduction gears 33 including a worm gearing mechanically connected to the safety device 31 by gear means, and a pinion 35 meshed with the rack 15 of the guide rail 11. The safety device 31 includes a shaft with a flange 32, and a gear 34 pressed by a spring and brought into a frictional engagement with the flange 32, and it is made so that the gear 34 idles and the rotation of the motor 29 is not transmitted to the pinion 35 when the pinion 35 receives a force larger than a frictional force existing between the gear 34 and the flange 32. A rotary encoder 36 is connected to the pinion 35 through gear means to produce signals corresponding to the travelling distance of the carriage 3. As previously stated, the back roller 23 is mounted on the bracket 37. The bracket 37 is fitted in a groove 38 made in the side portion of the housing 25 and separably secured thereto by screw means.

The carriage 3 can run on the guide rail 11 according to the rotation of the motor 29 and be stopped at any position.

Figure 2:
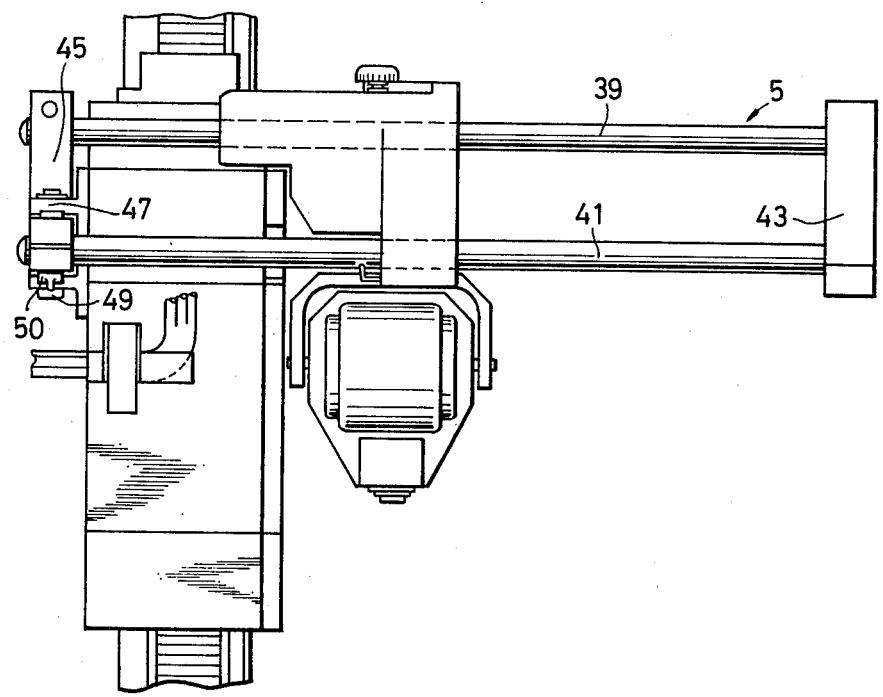
FIG. 2 is a plane view of the scanner in FIG. 1.

As shown in FIG. 2, the guide arm 5 comprises two rods 39, 41 arranged in parallel to each other, a tie member 43 tying the rods 39, 41 at one end of the rods 39, 41, and an L-shaped connecting member 45 which connects the rods 39, 41 to the carriage 3. The L-shaped connecting member 45 which secures thereto the end portions of the rods 39, 41 by bolt and nut means 50, is mounted rotatably on a bracket 47 secured to the side of the carriage housing 25 by a pin 49, whereby the guide arm 5 can pivot or swing around the pin 49 in a plane perpendicular to the travelling direction of the carriage 3. As shown in FIG. 3, the guide rods 39, 41 are arranged with horizontal and vertical spacings to each other when the carriage 3 is disposed horizontally. The guide arm 5 arranged in such that manner is mechanically stable and minimized in its deformation even when a rotating moment is applied to the guide arm 5.

The probe holder 7 slidably mounted on the guide arm 5 through ball bearings (not shown) will be described more in detail referring to FIGS. 4 and 5. The probe holder 7 comprises a holder housing 51 and a probe holding unit 52. The holder housing 51 has an upper arm portion 53 slidably mounted on the guide arm 5, and a lower arm portion 55 supporting the probe holding unit 52. The probe holding unit 52 comprises a ring-shaped member 61 embracing the periphery of the probe 9, a U-shaped member 65 connected to the ring-shaped member 61 and a rotatable shaft 67, one end of which is secured to the ring-shaped member 61 and the other end is rotatably supported by the lower arm portion 55 of the holder housing 51. The lower arm portion 55 has a pair of bearings 59. The rotatable shaft 67 of the arm holding unit 52 is inserted in the bearings 59, and it has a flange portion 68 at the intermediate portion which is sandwiched by a pair of springs 72 inserted in the lower arm portion 55 through spring holders 70, whereby the axial movement of the rotatable shaft 67 is restricted while it is rotated freely.

The probe 9 is fitted in the ring-shaped member 61 and secured thereto by a screw means 69. The probe 9, supported by the probe holder 7 in such a manner can be moved freely on the guide arm 5 by a manual operation. The probe 9 can be pivoted around the pin 63 and the rotatable shaft 67 which are crossed at a right angle on a plane slightly spaced from a surface to be inspected.

A position of the probe holder 7 on the guide arm 5 is measured by a rotary encoder 71. As shown in FIG. 5, the rotary encoder 71 is fastened to the holder housing 51 through a mounting member 73. The rotary encoder 71 has a rotatable shaft on which a pinion 75 is secured. The pinion 75 is meshed with a rack 40 formed on one 39 of the guide rods of the arm 5, whereby movement of the probe holder 7 is transmitted to the rotatable encoder 71.

A push button 77 for driving the motor 29 is provided on an upper portion 76 of a projection of the ring-shaped member 61. When the push button 77 is pushed, the probe 9 moves circumferentially by one pitch which is, for example, 6 mm corresponding to about 70% of the width of a surface to be inspected by scanning the probe 9 once. Namely, in FIG. 3, a movement of the motor 29 is transmitted to the pinion 35 through the safety device 31 and the gears 33. The movement of the pinion 35 causes the carriage 3 to move circumferentially on the guide rail 11 by a distance corresponding to the above mentioned one pitch. The movement of the carriage 3 is transmitted to the rotary encoder 37, and the rotary encoder 37 measures a circumferential position of the probe 9. An axial movement of the probe 9 on the pipe 2 is performed by manually moving the probe holder 7 on the guide arm 5. The axial movement of the probe 9 is transmitted to the rotary encoder 71 through the rack 40 of the guide arm 5 and the pinion 75 meshed therewith whereby the distance corresponding to the axial movement or shift is measured by the rotary encoder 71.

When the scanner 1 is used to inspect a welding portion 4 and a portion adjacent thereto as shown in FIG. 1, first, the guide rail 11 is mounted on the pipe 2 adjacent to a region to be inspected, that is, adjacent to the welding portion. Next, the scanner 1 is installed on the guide rail 11, whereby it is ready for operation. The probe 9 is positioned at a proper circumferential position of the pipe 2 by travelling circumferentially with the carriage 3 with the push button 77 being operated. Under this condition, an operator moves axially the probe holder 7 to inspect the pipe 2 while pressing the probe 9 on the surface to be inspected. After that, the carriage 3 is transferred by the motor 29 by one pitch, with the push button 77 being pushed. At the peripheral position, the probe 9 is moved axially as abovementioned. All the surface to be inspected is inspected by repeating the abovementioned operations. The probe 9 accurately follows even the curved surface of a bent pipe. When the probe 9 is moved axially while it is pressed on the curved surface of the bent pipe, the guide arm 5 supporting the probe holder 7 is pivoted or swung about the pin 47 and the probe 9 also is pivoted or rotated about the rotatable shaft 67 and the pin 63, according to the curvature of the curved surface, whereby the probe 9 faces always the surface to be inspected. When the probe 9 is moved in the peripheral direction, even if the carriage 3 is moved strictly circularly around the bent pipe, the probe 9 is not moved on the same track. Therefore the probe 9 follows the curved surface to be inspected through pivotal movement of the guide arm 5 about the pin 47, and pivotal movements of the probe 9 about the rotatable shaft 67 and the pin 63.

Peripheral and axial scanning distances of the probe 9 are measured by the rotary encoders each rotating according to the movements of the carriage 3 and the probe holder 7 as abovementioned.

In case of performing the ultrasonic flaw detection of the pipe 2 or the like, embraced by a heat insulating material, only the heat insulating material on the side of the welded part 4 may be detached from the pipe 2 in an amount corresponding to the length of the arm 5. Accordingly, the operation of detaching the heat insulating material for installing the scanner 1 can be readily executed in a short time. The danger of exposure of the operator lessens to that extent. The probability at which an obstacle exists in the movement of the probe 9 is lowered in accordance with the smallness of the quantity of detachment of the heat retaining material.

When, in performing the flaw detection of the curved surface part, the position of the probe 9 in the axial direction of the pipe 2 is judged from only the measured value of the rotary encoder 71, an error takes place.

Figure 7:
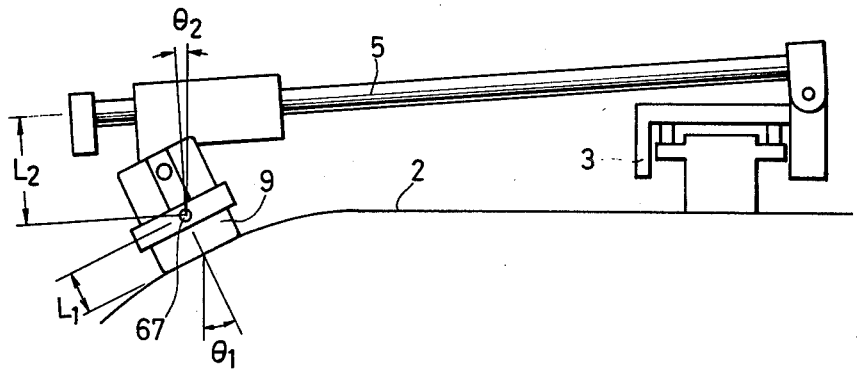
FIG. 7 is schematic diagram of the scanner shown in FIG. 1 for explanation of position correction.

This is because the arm 5 and the probe 9 pivot. In order to find an exact position of the probe 9, the sum between a component $L_1 \sin \theta_1$ ascribable to the pivoting of the rotatable shaft 67 and a component $L_2 \sin \theta_2$ ascribable to the pivoting of the arm 5 as indicated in FIG. 7 is added to or subtracted from the measured value of the rotary encoder 71.

Figure 6:
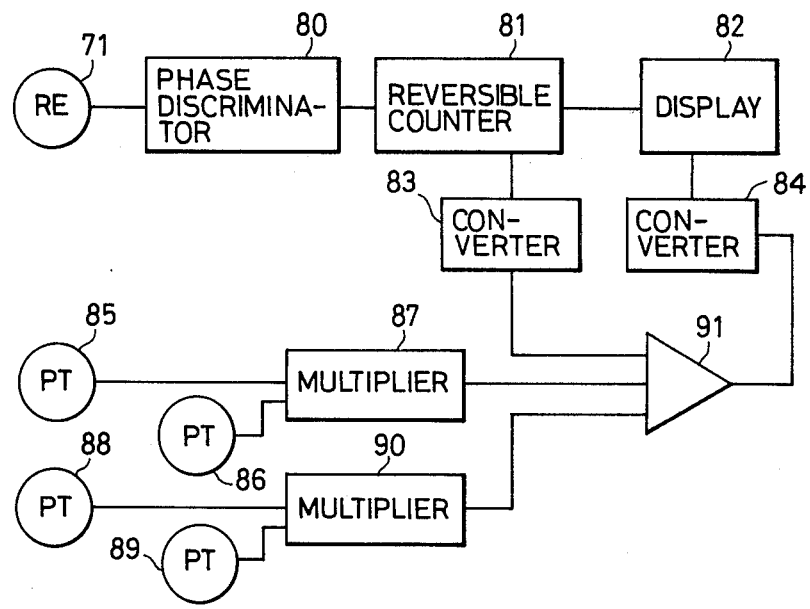
FIG. 6 is a block diagram of a position correction circuit employed in a scanner according to the invention.

Such method of correction for the axial position will be explained with reference to FIG. 6. Pulses generated from the rotary encoder 71 pass through a phase discriminator circuit 80 for deciding a direction, and are thereafter counted by a reversible counter 81. Although not shown, a potentiometer 85 for measuring the angle $\theta_1$ is mounted on the housing 51. Further, a potentiometer 88 for measuring the angle $\theta_2$ (inclination of the arm) is mounted on the carriage 3 for measuring the inclination. The measurement signal of the potentiometer 85 is transmitted to a multiplier unit 87. The multiplier unit 87 receives a signal from a potentiometer 85 in which the length $L_1$ between the pin 67 and the lower face of the probe 9 is set. The operation of $L_1 \sin \theta_1$ is executed in the multiplier unit 87. The measurement signal of the potentiometer 88 and a signal from a potentiometer 89 for setting the length $L_2$ between the arm 5 and the pin 67 are applied to a multiplier unit 90 to execute the operation of $L_2 \sin \theta_2$. The signals from the multiplier units 87 and 90 and also a signal obtained by converting an output of the reversible counter 81 by means of a converter 83 are respectively applied to an adder unit 91 and added therein, whereby the exact position of the probe 9 can be evaluated. After going through a converter 84, an output from the adder unit 91 is displayed on a coordinate value display unit 82 together with the circumferential position measured by the rotary encoder 36. It is also possible that, without making the correction as stated above, the signal of the reversible counter 81 is transmitted directly to the coordinate value display unit 82 through the change-over of a switch.

Another embodiment of the scanner according to the invention will be described hereinafter in detail, referring to FIG. 8. This embodiment differs from the above-mentioned embodiment mainly in a construction of a probe holder 7A, the probe holder 7A is suitable for axially transferring the probe 9 one pitch by one pitch by manual operation.

Figure 4:
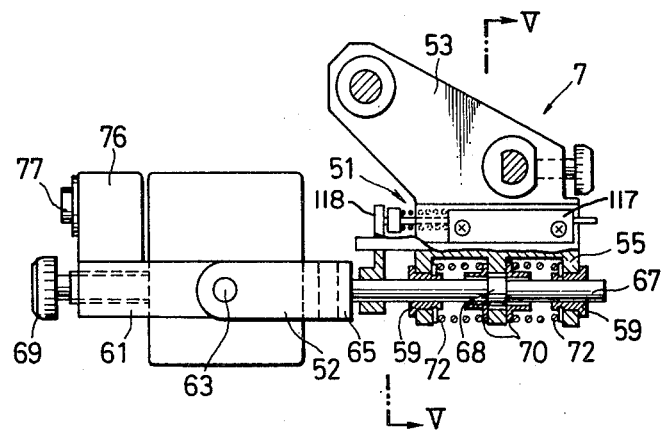
FIG. 4 is a sectional view of the scanner taken along a line IV—IV of FIG. 1.
Figure 5:
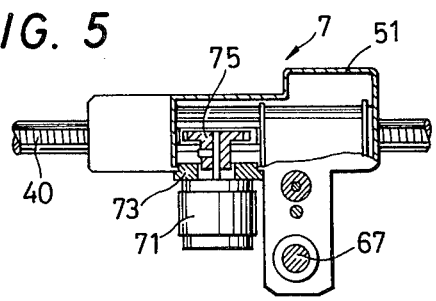
FIG. 5 is a sectional view of the scanner taken along a line V—V of FIG. 4.

In FIG. 8 showing a sectional view of the probe holder 7A taken along the same direction as in FIG. 1, a holder housing 51A moving slidably on the guide rods 39, 41 of the guide arm 5 holds the probe 9 in the same manner as in FIG. 4. A shaft 95 with knob is rotatably mounted on both the holder housing 51A and a bearing supporter 96 fixed to the holder housing 51 through bearings 97, and it is provided with a pinion 98, the rotation of which is transmitted to the rotary encoder 71 through gears to measure a scanning distance of the probe holder 7A on the guide arm 5. A shifter 94 is provided on the end portion of the shaft 95 with the knob. The shifter 94 comprises a disc 99 fixed to the end of the shaft 95 and a ball holder 100. The disc 99 has a plurality of ball receiving grooves 101 formed therein, two adjacent grooves determine an axial scanning pitch of the probe 9, for example 6 mm. The ball holder 100, which is cylindrical, is rotatably fitted on the knob shaft 95. The ball holder 100 is provided with one hole which is spaced from the axis thereof and extends axially. In this hole, a ball 106 is inserted loosely, and pressed on the disk 99 by a spring 102. The ball holder 100, furthermore, has another hole 110, formed perpendicularly to the axis of the ball holder 100, and receiving a pin 103 which is inserted in a pin holder 104 secured to the probe holder 51A. The pin 103 has a knob 105 fixed to one end thereof, and it is pressed by a spring 107 so as to fit in the hole 110 of the ball holder 100.

Under this condition, when the knob shaft 95 is rotated by manual operation, the ball 106 goes out from the groove 101, and enter the adjacent next groove 101, whereby the probe holder 7A is shifted by one pitch, and the distance shifted is measured by the rotary encoder 71. The probe 9 or the probe holder 7A can be shifted precisely one pitch by one pitch by repeating such operation.

When it is intended to release the probe holder 7A from the shifter 94, the knob 105 is pulled leftwards on FIG. 8 to take off the pin 103 from the hole 110 by about the length of a pin 111, and then rotated by a certain angle, whereby the pin 111 comes out of a groove 112 formed in the knob 105 so that the pin 103 is kept from the hole 110, and the probe holder 7A can be freely shifted.

The probe holder 7A with the shifter 94, for example in the case of inspection of a pipe, of which a portion to be inspected is shorter in its axial length and longer in its circumference, is shifted by one pitch by the manual operation as abovementioned as for axial transfer of the scanner 1, while circumferential shifting of the scanner 1 is performed by driving the motor 29, with the probe 9 being manually pressed on the portion to be inspected. By repeating the axial shift and the circumferential transfer, all the portion to be inspected is inspected effectively.

As mentioned previously, the circumferential scanning of the probe 9 is carried out by the carriage 3. The operation is performed while pressing the probe 9 on the surface to be inspected and an effective inspection can be carried out if the scanning speed changes in proportion to the force applied to the probe 9 toward the scanning direction. In order to carry out this, a direct current motor 29A for the motor 29 may be used, and there are provided a potentiometer 117 changing electric currents fed to the motor 29A, and an amplifier 116 for amplifying the electric currents, as shown in FIG. 9. The potentiometer 117, as shown in FIG. 4, is mounted on the holder housing 51, and actuated by a lever 118 mounted on a shaft 67. In this construction, the shaft 67 compresses the spring 72 and the lever 118 actuates the potentiometer 117 whereby the motor 29A is driven. As the probe 9 is further pushed, the resistance of the potentiometer 117 changes to increase electric current to the motor 29A whereby the scanning speed increases. Thus, the scanning speed of the carriage 3 is freely changed by a manual operation, and effective inspection can be achieved.

Further another embodiment of a scanner according to the invention will be described hereinafter in detail, referring to FIGS. 10 to 13.

In FIG. 10, a carriage 132 or a circumferentially driving apparatus is provided with a plurality of guide rollers 145, 146 and a gear 150. The guide rollers 145 sandwich an annular guide rail 131 up and down, and the guide rollers 146 sandwich the guide rail 131 from opposite sides, so that the carriage 132 can travel on and along the guide rail 131. The gear 150 is meshed with rack 147 formed on the guide rail 131. The gear 150 is driven by a motor 152 through a worm 153 and gears 148, 149. Rotation of the gear 150 allow the carriage to move circumferentially on the guide rail 131. Rotation of the motor 152 is transmitted to a rotary encoder for measuring a circumferentially travelling amount of the carriage 132 through the gear 148, 149 and a gear 154.

A probe holder 134 having a driving apparatus which has a shifter as previously described in FIG. 8 is mounted slidably on a guide arm. The arm, as best shown in FIG. 11, comprises an upper rod 155 and two lower rods 136 each extending in a transverse direction of the travel direction of the carriage 132, and a pair of tying members 154 for tying ends of the rods 155, 136. The upper rod 155 is supported by the carriage 132 with a pin 140 fired to the carriage so that the arm can swing or pivot in a plane transverse the travel direction of the carriage 132. The probe holder 134 is slidably mounted on the lower rods 136, and has a rotary encoder 135, to which axial movement of the probe holder 134 is transmitted through a pinion 156 meshed with a rack formed on the rod 136, gears 157, 158. On the probe holder 13A, a rotatable shaft 139 is rotatably mounted, extending in the travel direction of the carriage 132. A probe 124 is fitted in a probe mounting member 138 which is rotatably connected to the rotatable shaft 139 by a pin 159 so that the probe can be pivoted about two axes as shown by arrows in FIGS. 10 and 11. A knob 137 of the shifter is for shifting the probe 124 intermittently with an interval of one pitch. The pitch is taken in such a way that two adjacent tracks of the probe 124 are overlapped partially.

Figure 12:
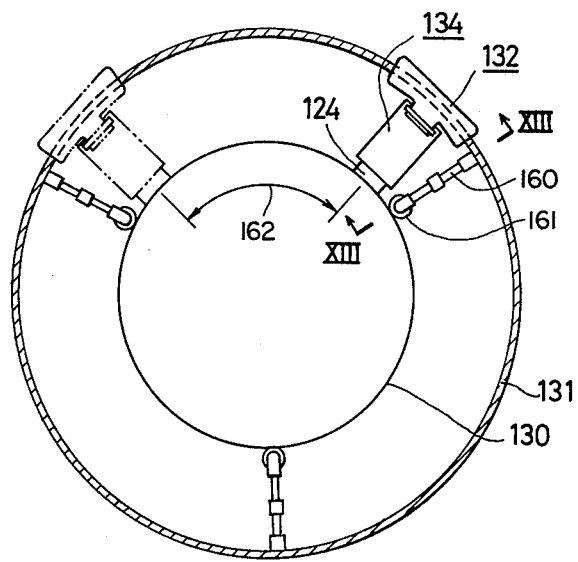
FIG. 12 is a schematic diagram of the scanner shown in FIG. 10 and a guide rail for explanation of their operations.
Figure 13:
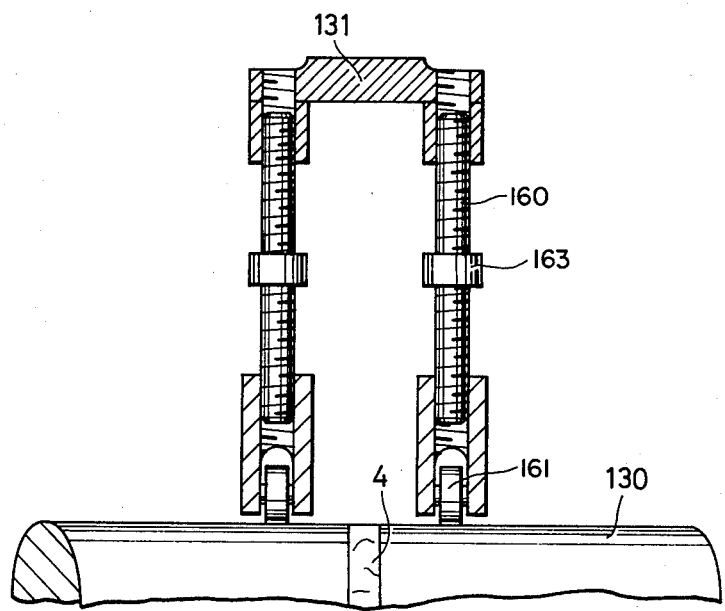
FIG. 13 is a sectional view of the guide rail taken along a line XIII—XIII.

In FIGS. 12 and 13, the annular rail 131 is mounted on a piping 130 to be inspected through three (3) poles 160 with spacing adjustable devices 163. The poles each have a roller 161, whereby the guide rail 131 can be transferred circumferentially.

In case where ultrasonic flaw detection of the piping 130 is effected, the probe 124 is gripped by an operator's hand, and shifted manually between the tying member 154 and the opposite tying member 154. The probe 124 is held so as to be easily inclined axially and circumferentially so that the probe 124 accurately follows and contacts even a curved and complicated surface of an object to be inspected, and can emit a proper ultrasonic beam on the surface to be inspected. In a circumferential scanning for flaw detection, the carriage 132 is transferred circumferentially on the rail 131 by the motor 152. Axial and circumferential positions are automatically measured by the rotary encoders 135 and 133, and signals corresponding to the positions are sent to a display and a control apparatus, wherein the position of the probe can be automatically displayed. Of course, the results of the ultrasonic flaw detection scanning are recorded. In the case of circumferential ultrasonic flaw detection scanning, as shown in FIG. 12, the travelling range is limited by the poles 150, but the rail 131 is constructed so as to move circumferentially, whereby the ultrasonic flaw detection scanning can be performed over the surface. As regard positioning of the probe 124 after the movement of the annular rail 131, a precise position can be detected by setting the probe 124 on the marked points to reset the position display device after marking several points on this surface of the object to be inspected, and setting the probe 124 on the marked points.

Thus, the scanner for piping according to this embodiment is constructed in such a way that the probe 124 can be inclined axially and circumferentially to contact with the surface, therefore inspection can be performed on welding portions in straight pipes, elbows, valves, pumps, and welding portions formed by various combinations of them, and its application range is increased. Furthermore, in accordance with the invention skilled inspectors are exposed less to radioactivity in the case of inspection of radioactive piping, and a great reduction of time necessary for analyzing inspecting results can be obtained.

Further, in the case of the inspection of a pipe provided with heat retaining or insulating material, since the annular guide rail is arranged on a surface to be inspected, the amount of the heat insulating material to be removed is reduced greatly, compared with for example the prior art discussed.

What is claimed is:

1. A semi-automatic scanner for ultrasonic flaw detection comprising:
    carriage means travelling on a guide rail;
    arm means extending in a direction transverse to the travel direction of said carriage means and mounted on said carriage means for pivotal movement in a plane transverse to the travel direction;
    probe holder means slidably mounted on said arm means;
    probe means pivotably mounted by said probe holder means so that said probe means follows a curved surface to be inspected, said probe holder means including first means for enabling pivoting movement of said probe means about a first axis transverse to the travel direction of said carriage means, and second means for enabling pivoting movement of said probe means about a second axis transverse to said first axis, said carriage means being driven by motor means, and said probe holder means being slidably moved along said arm means by a manual operation; and
    means for controlling the driving speed of said motor means in proportion to the force applied to said probe means.

2. The scanner as defined in claim 1, wherein said probe holder means includes means for allowing relative movement to said probe holder means, and said controlling means comprises a potentiometer provided in said probe holder means and electrically connected to said motor means, and a lever for actuating said potentiometer according to the movement of said probe means.

3. A semi-automatic scanner for ultrasonic flaw detection comprising:
    carriage means travelling on a guide rail;
    arm means extending in a direction transverse to the travel direction of said carriage means and mounted on said carriage means for pivotal movement in a plane transverse to the travel direction;
    probe holder means slidably mounted on said arm means;
    probe means pivotably mounted by said probe holder means so that said probe means follows a curved surface to be inspected, so that said probe means follows a curved surface to be inspected, said probe holder means including first means for enabling pivoting movement of said probe means about a first axis transverse to the travel direction of said carriage means, and second means for enabling pivoting movement of said probe means about a second axis transverse to said first axis, said carriage means being driven by motor means, and said probe holder means being slidably moved along said arm means by a manual operation, and intermittent shifter means for axially shifting said probe means along said arm means one pitch by one pitch, said intermittent shifter means including a rotatable shaft engaged with said arm means through transmission means so that shifting movement of said probe holder means is changed to rotational movement, a disc secured to said rotatable shaft and having ball receiving grooves spaced from one another by a distance corresponding to said one pitch, and a spring holder having a spring and ball pressed on said disc to prevent said rotatable shaft from freely rotating and to allow the rotation of said rotatable shaft when a rotary force applied to said rotatable shaft exceeds a predetermined value.

4. The scanner as defined in claim 1 or 3, wherein said first and second axes are perpendicular.

5. A semi-automatic scanner for ultrasonic flaw detection comprising:

carriage means travelling on a guide rail mounted on the surface of an object to be inspected, said carriage means having spaced side portions;

arm means having a plurality of rods each extending in parallel to each other in a direction transverse to the travel direction of said carriage means, said arm means being mounted on said carriage means at an axially central portion so as to be pivotable about an axis extending in the travel direction of said carriage means;

probe holder means slidably supported by said arm means for sliding movement from one side portion of said carriage means to the other side portion of said carriage means; and a probe mechanically connected to said probe holder means.

6. The scanner as defined in claim 5, further including a first rotary encoder mounted on said carriage means and driven by a roller through gear means, and a second rotary encoder mounted on said probe holder means and engaged with one of said rods so as to rotate in response to axial movement of said probe holder means on said arm means.

7. The scanner as defined in claim 5, including tying means for tying said rods, said tying means including a L-shaped member having two ends, said rods being secured to the end portions of said L-shaped member, respectively.

8. The scanner as defined in claim 5, wherein said probe holder means includes a holder housing and a probe holder unit, said probe holder unit including a ring-shaped member for fitting therein said probe, and means for connecting said ring-shaped member to said holder housing to be pivotable about two axes transverse to each other.

9. The scanner as defined in claim 5, further including a guide rail circumferentially travelling on a pipe to be inspected, said guide rail having at least three poles with rollers at their ends.

10. The ultrasonic flaw detector as defined in claim 9, wherein each of said poles is provided with adjustable means for adjusting the spacing between said guide rail and said pipe.

* * * * *